United States Patent [19]

Austin

[11] Patent Number: Plant 7,214

[45] Date of Patent: Apr. 10, 1990

[54] ROSE PLANT — AUSBUFF

[75] Inventor: David C. H. Austin, Albrighton, England

[73] Assignee: David Austin Roses, Albrighton, England

[21] Appl. No.: 259,277

[22] Filed: Oct. 18, 1988

[51] Int. Cl.[4] ..... A01H 5/00

[52] U.S. Cl. ..... Plt./1

[58] Field of Search ..... Plt. 1, 7, 22

*Primary Examiner*—James R. Feyrer

*Attorney, Agent, or Firm*—Ladas & Parry

[57] ABSTRACT

A new variety of rose plant of the shrub class distinctive in its character by its fully double, soft apricot yellow flowers with abundant, continual blooming and the unusual blend of coloring and shaping of the flower.

1 Drawing Sheet

BACKGROUND OF THE INVENTION

The present invention relates to a new and distinct variety of shrub rose, a seedling resulting from a definite effort to produce an improvement in this class of roses.

SUMMARY OF THE INVENTION

Primary features of this new variety which connote a distinctive advance over existing types are the vigorous abundant and continual blooming taken with the perfection of the fully double flowers of an old-fashioned type more particularly apparent in the accompanying illustration of a specimen thereof.

BRIEF DESCRIPTION OF THE DRAWING

The drawing depicts, from side view, stems, foliage, flower buds and flowers in various stages of developments.

DETAILED BOTANICAL DESCRIPTION

The following is a detailed description of the new variety, colour terminology being in accordance with the "Methuen Handbook of Colour" published by Eyre Methuen Ltd. (1963).

Variety denomination: (in accordance with the UPOV Convention): Ausbuff (Trade name English Garden).

Type: Hardy; bush; outdoor; seedling; for cut flowers and garden decoration.

Class: Shrub.

Propagation: Holds its distinguishing characteristics through succeeding propagations by budding.

The rose plant was grown at Albrighton, Nr. Wolverhampton, England and was derived as follows:

Female parent (seed parent): Lilian Austin.

Male parent (pollen parent): (Seedling × Iceberg).

The operation of the artificial pollination is therefore expressed by the following (Lilian Austin × (Seedling × Iceburg)).

The following observations are made of specimens grown outdoors in England.

Plant Description

Plant:

*Height.*—90 cm on average.

*Habit.*—Upright and bushy.

Branches:

*Colour.*—Young stems: Deep Green 29 E8, Adult wood: Deep Green 30 E8.

Leaves:

*Stipules.*—Medium to Light Green. Medium width. Glandular hairy edge.

*Petiol.*—Upper side — Grooved Medium Green. Under side — Rounded occasional medium thorns — glandular hairy.

*Folioles.*—Number 5, 3 at base of inflorescence. Shape — ovate, Serration — dentate, Texture — medium.

*General effect.* —Fairly dense Matt Green — semi-glossy.

*Colour.*—Young foliage — Upper side — Deep Green 30 E8, tinged with red. Under side — Reddish-Green. Adult foliage — Upper side — Dark Green 29 F8. Under side — Greyish Green 29 E6.

Hips and seeds: This variety does not produce seeds in all gardening conditions, only when cross-pollinated.

Inflorescence

Number of flowers: One or two.

Peduncle: Straight, rigid, medium green sparsely glandular aciculas.

Length: 8 cm on average.

Sepals: Upper side: Finely hairy — Light Green. Under side: Light Green, with glandular hairs along central vein or finely hairy at edges, with 0–3 narrow lobes.

Bud.

*Shape.*—Oval, pointed.

*Length.*—3 cm. on average.

*Size.*—Medium.

*Color.*—When opening. Upper side: Very deep Yellow, 1 A8 at base merging to Reddish Yellow 4 A7 at outside. Under side: Very Deep Yellow merging to Very Deep Red 9 C7.

Flower:

*Shape.*—Slightly quartered — flattish.

*Diameter.*—13 cm on average.

*Colour.*—When opening. Upper side: Deep yellow 3 A8 turning to Pale Yellow 2 A2. Under side: Deep yellow 3 A8 turning to Very Deep yellow 2 A2. When blooming: Outer petals — Deep Yellow 3 A6 turning to very Pale Yellow 3 A2. Upper side — Inner petals — Yellow 3A7, turning to Pale Yellow 2 A3. Under side: Outer petals — Yellow 3 A6 turning to very Pale Yellow/Cream 3 A2. Inner petals — Yellow 3 A7 turning to Pale Yellow 2 A3. When finished blooming: Upper side: Deep Yellow 2 A8 at base turning to Pale Yellow 2 A3 (petals fading to cream on the outside). Under side: Same as above.

*Fragrance.*—Light fragrance.

*Lasting quality.*—Very good.

Petals:

*Shape.*—Spatulate.

*Texture.*—Silky.

*Number.*—76.

*Cleaning.*—Good.

Reproductive organs

Stamens:

*Number.*—71.

*Anthers.*—Golden Yellow.

*Filaments.*—Golden Yellow — regular heights.

Pistils:

*Number.*—56 on average.

*Stigmas.*—Straw.

*Styles.*—White — fairly regular.

*Receptacle — Pale green with pale yellow Ridge — moderately deep cup.*

The development:

*Vegetation.*—Strong upright.

*Blooming.*—Continuous.

*Aptitude to bear fruits.*—Normal.

*Resistance to frost.*—Good.

*Resistance to diseases.*—Good.

I claim:

1. A new and distinct variety of rose plant of the shrub class, characterized as to novelty by its fully double, soft apricot-yellow flowers with abundant and continual blooming the unusual blend of colouring and shaping of the flower being substantially as shown and described.

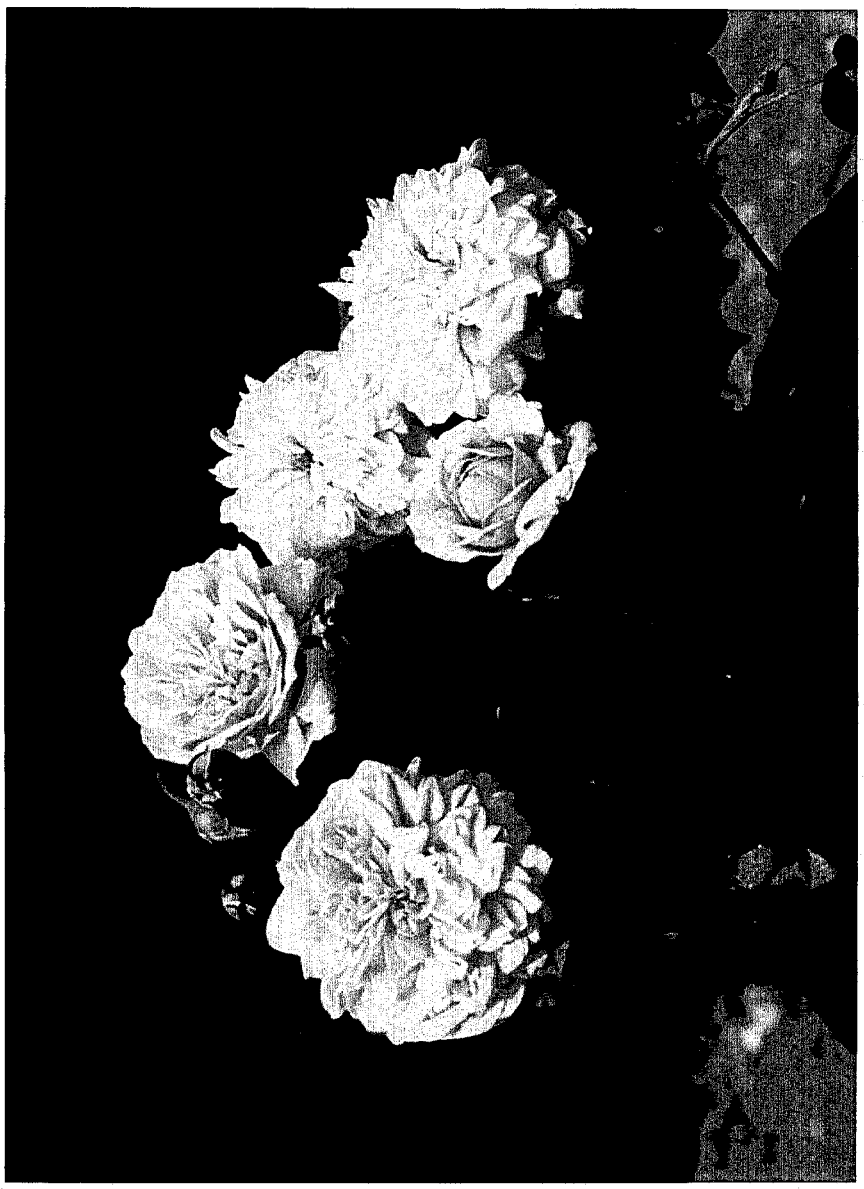

* * * * *